US00PP15294P3

(12) United States Plant Patent
Warren et al.

(10) Patent No.: US PP15,294 P2
(45) Date of Patent: Nov. 2, 2004

(54) CALLA LILY PLANT NAMED 'HOT CHOCOLATE'

(50) Latin Name: *Zantedeschia species*
Varietal Denomination: Hot Chocolate

(75) Inventors: Andrew G. F. Warren, Tauranga (NL); Jacobus J. P. Spaans, Tauranga (NL)

(73) Assignee: Bloomz Ltd. (NZ)

( * ) Notice: Subject to any disclaimer, the term of this patent is extended or adjusted under 35 U.S.C. 154(b) by 47 days.

(21) Appl. No.: 10/382,957

(22) Filed: Mar. 6, 2003

(65) Prior Publication Data

US 2004/0177423 P1 Sep. 9, 2004

(51) Int. Cl.[7] ..... A01H 5/00

(52) U.S. Cl. ..... Plt./263

(58) Field of Search ..... Plt./263

(56) References Cited

PUBLICATIONS

UPOV–ROM GTITM Computer Database, 2003/04, GTI Jouve Retrieval Software, citation for 'Hot Chocolate'.*

* cited by examiner

*Primary Examiner*—Kent Bell
*Assistant Examiner*—S. B. McCormick-Ewoldt
(74) *Attorney, Agent, or Firm*—Jondle & Associates P.C.

(57) ABSTRACT

A calla lily plant particularly distinguished by dark purple spathe and maculated leaves.

4 Drawing Sheets

Genus and species: *Zantedeschia* species.
Variety denomination: 'Hot Chocolate'.

BACKGROUND OF THE NEW PLANT

The present invention comprises a new and distinct cultivar of calla lily, botanically known as *Zantedeschia* spp, and hereinafter referred to by the cultivar name 'Hot Chocolate'. The new cultivar is asexually reproduced from vegetative cuttings and tissue culture resulting from the cross of the seed parent 'Cameo'×the pollen parent, a dark purple seedling that is an unnamed and unpatented proprietary line. The seed parent, 'Cameo,' differs from the observed plant, 'Hot Chocolate' in that the spathe is an apricot-salmon color. 'Hot Chocolate' has medium green arrow-shaped leaves while the pollen parent, the unnamed dark purple seedling, has more oval shaped and darker green leaves.

'Hot Chocolate' is a product of a planned breeding program intended to create new calla lily plants with a deep burgundy spathe.

The new cultivar was created in 1998 in Tauranga New Zealand and and has been asexually reproduced repeatedly by vegetative cuttings and tissue culture in New Zealand over a 3 year period. The present invention has been found to retain its distinctive characteristics through successive propagations; and this novelty is firmly fixed.

DESCRIPTION OF PHOTOGRAPH

This new calla lily plant is illustrated by the accompanying photographs which show blooms, buds, and foliage of the plant in full color, the colors shown being as true as can be reasonably obtained by conventional photographic procedures.

DESCRIPTION OF THE NEW CULTIVAR

Figure 1:
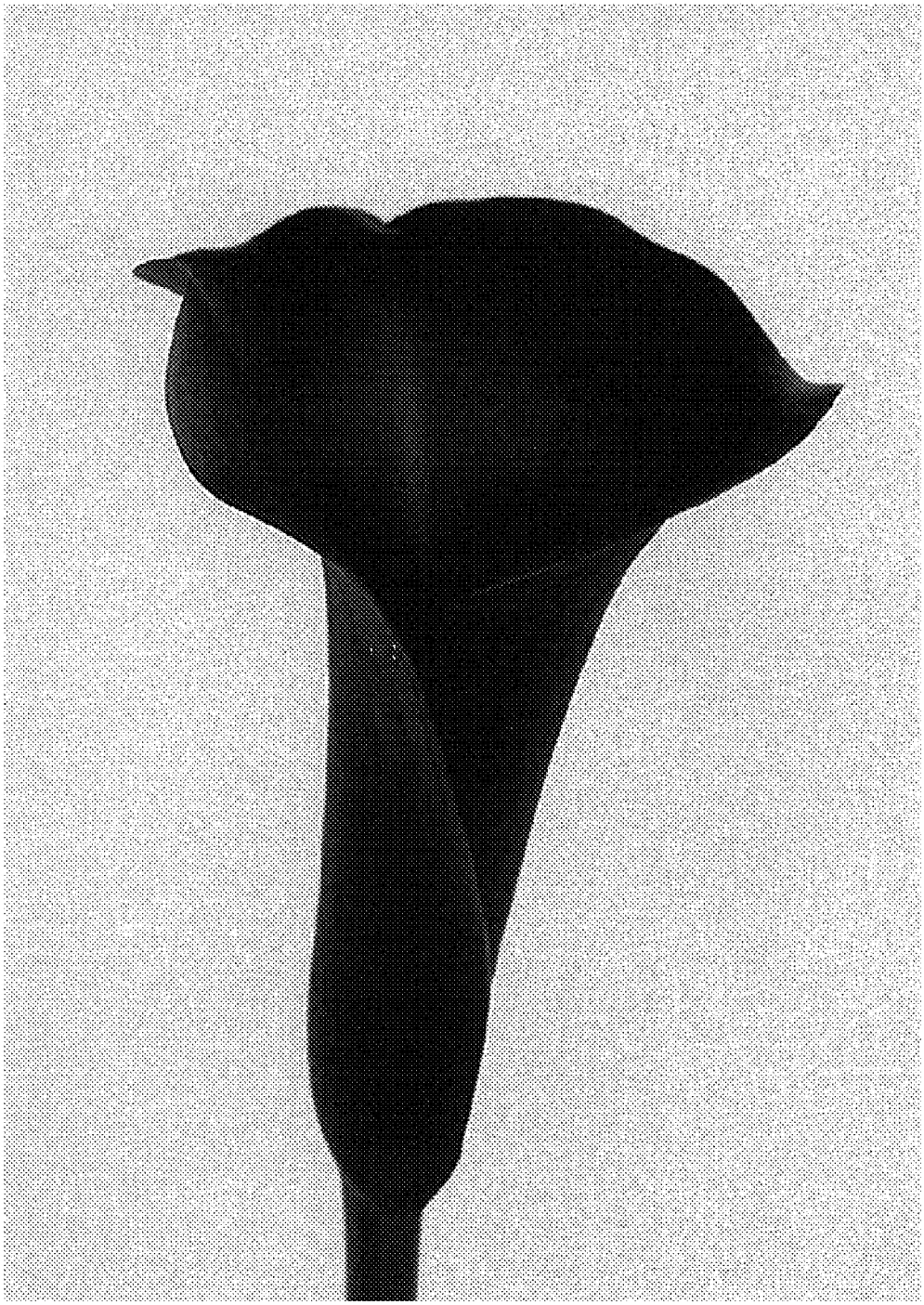
FIG. 1 shows the mature inflorescence.
Figure 2:
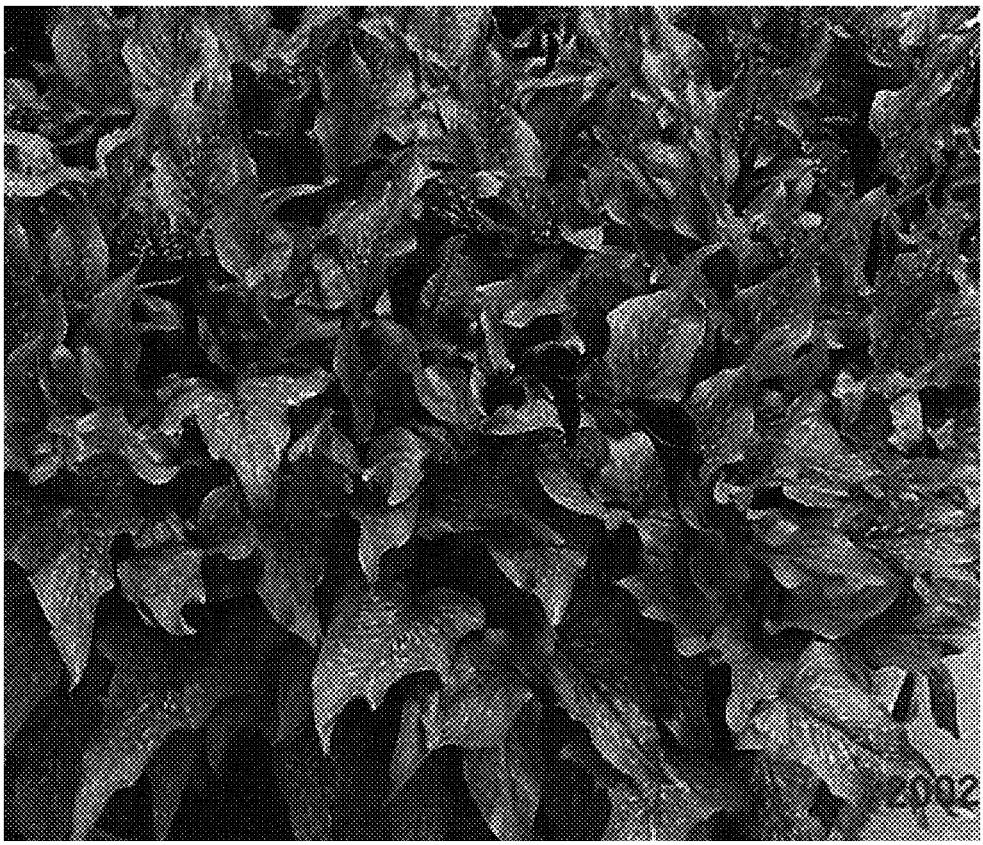
FIG. 2 shows the overall plant habit.
Figure 3:
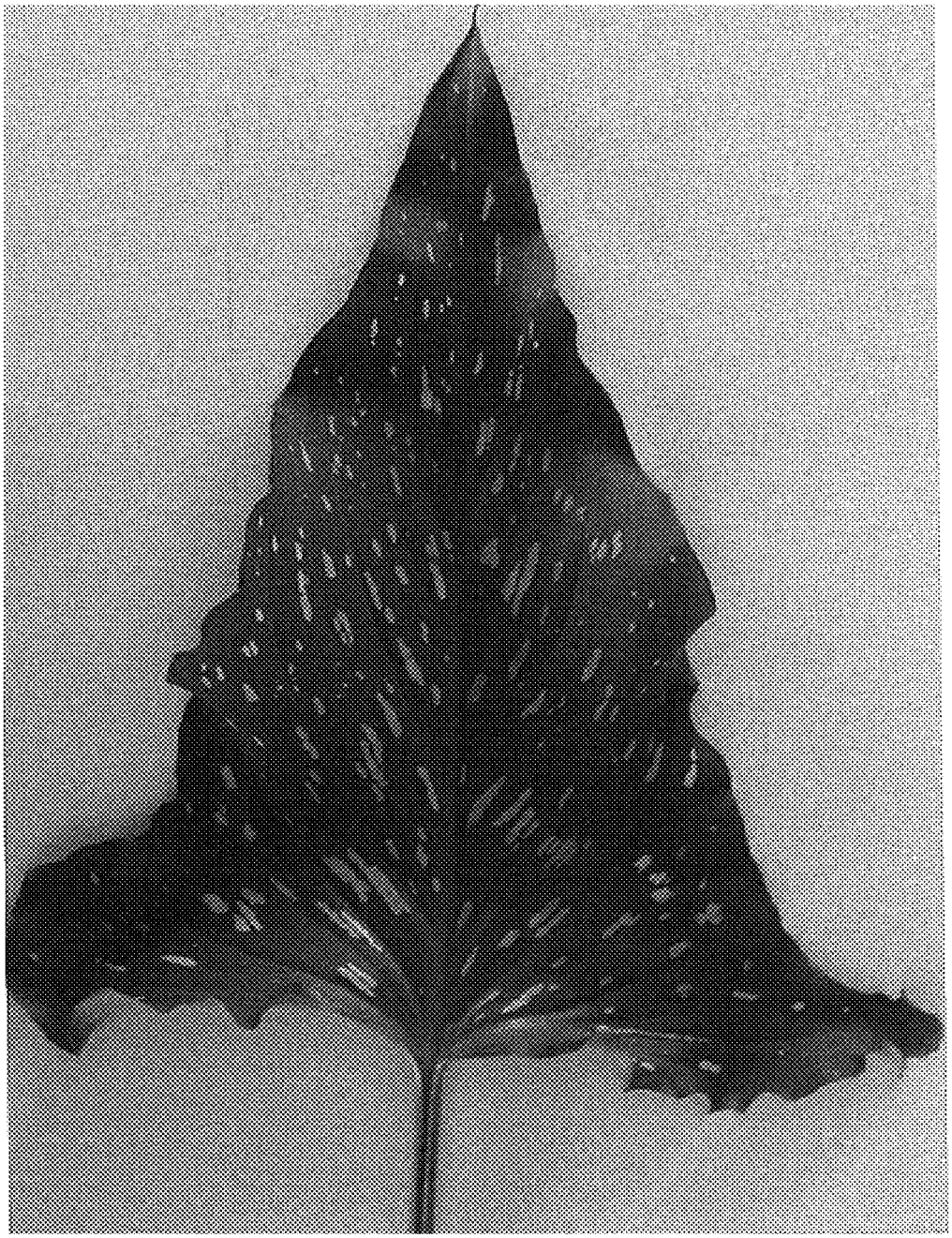
FIG. 3 shows the leaf.
Figure 4:
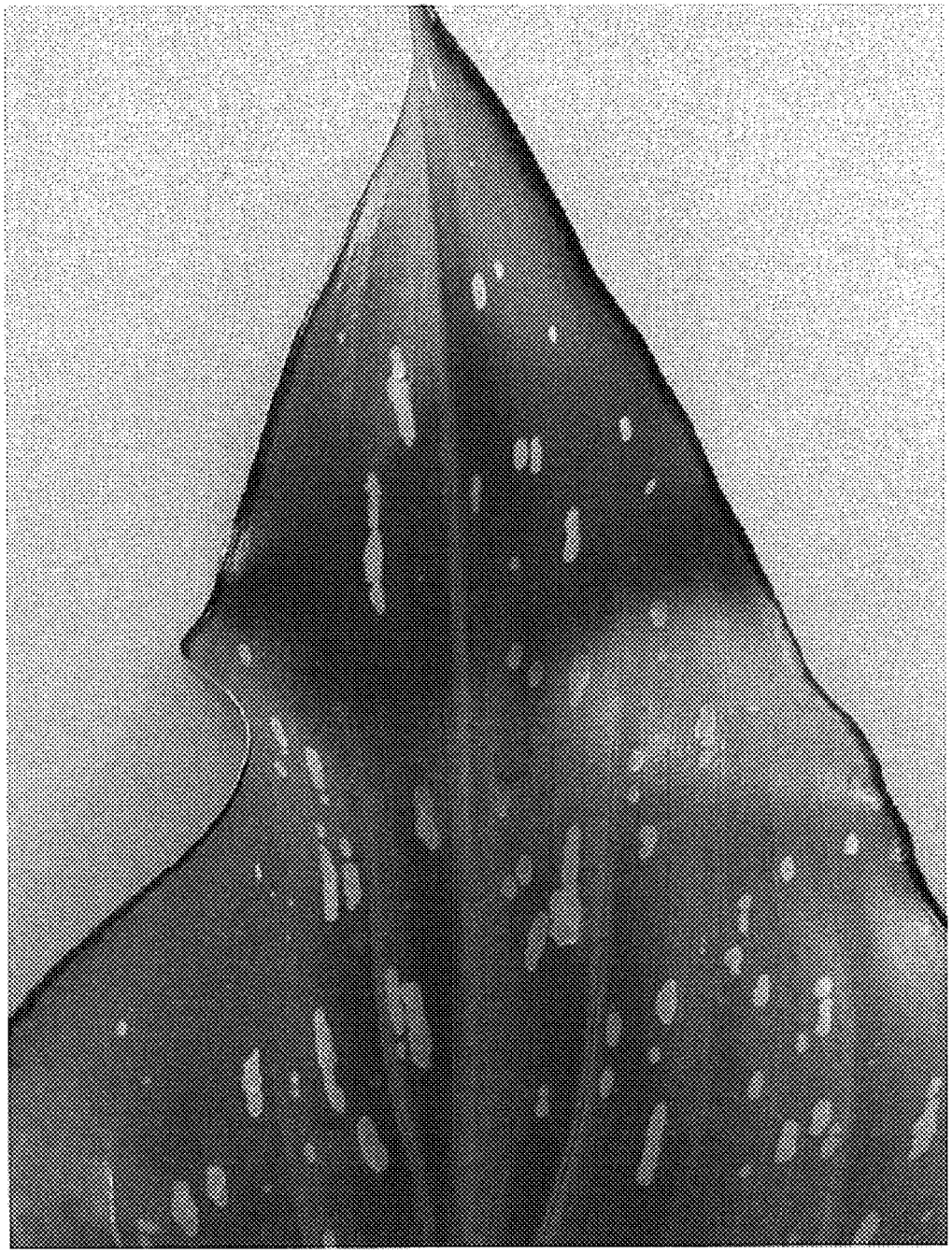
FIG. 4 shows a close-up of the leaf tip illustrating the margin colors.

The following detailed descriptions set forth the distinctive characteristics of 'Hot Chocolate'. The data which defines these characteristics were collected from asexual reproductions carried out in New Zealand. The plant history was taken on 2 year old plants based on a 4 cm diameter tuber under New Zealand Spring conditions. Color references are primarily to the R.H.S. Colour Chart of The Royal Horticultural Society of London (RHS).

THE PLANT

Classification:
- *Botanical.*—*Zantedeschia* spp.
- *Commercial.*—Calla lily.
- *Variety.*—'Hot Chocolate'.

Size:
- *Form.*—Erect.
- *Height of the leaf canopy above the soil.*—60–80 cm.
- *Height of top of inflorescence above the soil.*—60–90 cm.
- *Diameter.*—30–50 cm.
- *Number of inflorescence per tuber size.*—Tuber diameter 3 cm 1–2. Tuber diameter 4 cm 3–4. Tuber diameter 5 cm 4–6.

Branches:
- *Character.*—Strong.
- *Color.*—Upper is green RHS 146B; lower is dark purple RHS 184A; base is white RHS 155B.
- *Average number.*—3–4.

Leaves:
- *Size.*—Width 15–18 cm; length 25–30 cm.
- *Shape.*—Sagittate.

*Color.*—Upper is green RHS 137C; lower is green RHS 137C.
*Maculation* (*leaf spots*).—Medium density; white RHS 155C.
*Apex.*—Acute to apiculate.
*Margin.*—Moderately wavy.
*Margin color.*—Green RHS 137B with dark purple RHS 187A border.
*Veins.*—Pinnate.
*Surface quality.*—Leathery.

Petiole (leaf stalk):
*Length.*—40–50 cm.
*Color.*—Base is dark purple RHS 184A; upper is green RHS 144B.

Roots:
*Color.*—White.
*Branching.*—Not branched, attached to the top of the tuber at the apices.
*Disease resistance.*—No susceptibility noted to date.
*Pest resistance.*—No susceptibility noted to date.

THE INFLORESCENCE

Spathe (flower body):
*Size.*—Length 8–10 cm; width 6–8 cm.
*Color.*—Upper is dark purple RHS 187A; lower is black RHS 202A.
*Veins.*—Present, black RHS 202A.

Spadix (reproductive organs):
*Size.*—Length 4–5 cm; diameter 0.6–1.0 cm.
*Color.*—Base is dark purple RHS 187A; Upper is dark purple RHS 187B.
*Position relative to spathe.*—Upright.

Peduncle (flower stem):
*Size.*—60–80 cm.
*Color.*—Dark purple RHS 187A; upper is grey-green RHS 189A.

Reproductive organs:
*Location of female organs.*—Basal position of the spadix.
*Location of male organs.*—Upper position of the spadix.
*Perianth* (*the floral envelope — calyx and corolla*).—Conspicuous.
*Stamens.*—Not visible before pollen release.
*Pistil.*—20–40 per spadix; dark purple RHS 187A.

Miscellaneous:
*Time to produce a finished flowering plant.*—6–8 weeks.
*Lastingness.*—1–3 weeks.
*Fragrance.*—None.
*Fruit production.*—20–40 berries.
*Color.*—Predominantly dark purple RHS 187A.

COMPARISON WITH KNOWN CULTIVARS

When the instant plant is compared to 'Schwarzwalder' (U.S. Plant Pat. No. 11,001) the foliage is sagittate while 'Schwarzwalder' is ovate. Additionally, the peduncle of 'Hot Chocolate' is purple while 'Schwarzwalders' peduncles are green.

I claim:

1. A new and distinct cultivar of calla lily plant as shown and described herein.

* * * * *